United States Patent [19]

Ruggera et al.

[11] Patent Number: 4,527,550
[45] Date of Patent: Jul. 9, 1985

[54] HELICAL COIL FOR DIATHERMY APPARATUS

[75] Inventors: Paul S. Ruggera, McLean, Va.; Gideon Kantor, Garrett Park, Md.

[73] Assignee: The United States of America as represented by the Department of Health and Human Services, Washington, D.C.

[21] Appl. No.: 461,954

[22] Filed: Jan. 28, 1983

[51] Int. Cl.³ .............................................. A61N 1/40
[52] U.S. Cl. ................................. 128/1.5; 128/419 F; 219/10.79
[58] Field of Search ................ 128/1.3, 1.5, 82.1, 128/419 F, 804; 219/10.79

[56] References Cited

U.S. PATENT DOCUMENTS 4,066,065  1/1978  Kraus ...................................... 128/1.5
4,266,532  5/1981  Ryaby et al. ........................... 128/1.5

FOREIGN PATENT DOCUMENTS 1113156   11/1981  Canada .................................. 128/1.5
0039988   11/1981  European Pat. Off. ............. 128/1.3
2707574   8/1978   Fed. Rep. of Germany ....... 128/1.3
WO81/02841 10/1981 PCT Int'l Appl. ................. 128/804

Primary Examiner—Lee S. Cohen
Attorney, Agent, or Firm—Browdy and Neimark

[57] ABSTRACT

A deep-heating diathermy apparatus consisting of a hollow tube adapted to receive a part of the body, or other dielectric material to be treated. An rf coil coaxially surrounds the tube and is driven by an rf generator. The total wire length of the coil is approximately 0.7 to 1.3 (depending on specific electrical properties and volume of the treated material) times the wavelength of a basic driving frequency provided by the generator. The output of the generator is supplied to the coil via a 50-ohm coaxial cable and a matching impedance. The coil may be driven by frequencies corresponding to integral multiples of one-half the basic wavelength, to enable shifting the heat focus volume along the coil axis from the normal centered location on the axis produced by full-wave excitation.

14 Claims, 7 Drawing Figures

HELICAL COIL FOR DIATHERMY APPARATUS

FIELD OF THE INVENTION

This invention relates to diathermy apparatus, and more particularly to apparatus employing an improved diathermy coil adapted to receive a limb or other body portion for deep-heating treatment, such as hyperthermia in cancer therapy, bone healing, other types of medical applications requiring diathermy, or for industrial applications.

BACKGROUND OF THE INVENTION

Previously proposed systems of diathermy by exposure to radio frequency energy have not been satisfactorily successful in their applications to cancer therapy and other medical and industrial procedures because the prior systems do not efficiently heat lossy dielectric materials, do not deliver uniform cross-sectional heating, do not include self-supporting enclosure arrangements, produce excessive stray radiation, involve series resonance requiring an external capacitance connected in series with the diathermy coil, do not produce fields which are concentrated at the longitudinal center of the coil, and are not capable of delivering sufficient and uniform heat to deep-seated tumors.

The previously used diathermy systems are also unsatisfactory because they are not provided with an adequate limb or trunk-receiving diathermy therapy enclosure, do not provide uniform deep-heating in tissue (or other lossy dielectric material) undergoing diathermy treatment, do not concentrate the heat along a portion of the axis of the receiving enclosure, excessively heat surface tissue, and cause considerable discomfort to the patient.

Typical of these previously proposed systems are the devices disclosed in the following prior U. S. patents, found in a preliminary search of the prior art:

|          |           |
| -------- | --------- |
| Wappler, | 1,962,796 |
| Story,   | 2,503,779 |
| Gard,    | 2,515,211 |
| Lindahl, | 2,671,853 |
| Porterfield et al, | 3,375,468 |
| Beeston, | 3,408,598 |
| Jakoubovitch, | 3,571,644 |
| Mettler, | 3,747,013 |

SUMMARY OF THE INVENTION

The present invention typically comprises a limb- or trunk-receiving hollow tube, or similar coil support, with an rf coil wound coaxially thereon, so constructed and operated that it produces uniform deep-heating in tissue (or other lossy dielectric material) substantially axially located therein and focusses heat volume along the coil's axis, without excessively heating surface tissue. The coil is normally used under full wave operation at "coil wire-length" resonance, as opposed to the more widely known self-resonance of the coil. Under unloaded conditions (no tissue inserted into the coil), this has been found to occur at about three times the coil's self-resonant frequency during full wave operation. Under loaded conditions (tissue inserted into the coil), coil wire length resonance has been found to be dependent primarily on the length of wire used in winding the coil (not the length of the coil), and will occur only at one operating frequency for a given load placed in a given coil. During full wave loaded operation, depending on the specific electrical properties and volume of the tissue being treated, the length of wire necessary will range from 0.7 to 1.3 of the free-space wavelength of the desired operating frequency. For example, using a full-length, arm sized, fat-muscle phantom in a full length arm coil, the length of wire used is 0.75 of the free-space wavelength of the desired operating frequency; similarly, using a trunk sized, fat-muscle phantom in a body length (head, trunk, and legs) coil, the length of wire used was 1.19 of the free-space wavelength of the desired operating frequency. To obtain the high rate of heating uniformity in cross-section, it is essential that coil wire length be realized prior to application of power, and that the coil length is preferably 4 times the coil diameter for the particular load being heated in a given coil. Since the feed cable to the coil is coaxial, a standing wave ratio (SWR) meter, or similar device (directional couplers with power meters), can be easily attached to the feed cable. Using low radio frequency (rf) power, rather than the eventual high rf power for heating, the load is inserted into the coil and the SWR meter indication noted. Three means for obtaining coil wire length resonance are then possible. They are as follows: (1) If the load does not change, an industrial process for example, then the coil is built so that the wire length is at least 1.3 times the wavelength of the desired operating frequency. Using low power, with the load inserted, the coil is unwound until the SWR meter nulls (achieves the lowest reading). Once this occurs, coil wire length resonance exists at full wave operation and power is applied for heating. (2) If the load is variable, such as treatment of human arms, then a coil wound with wire length equal to 1.3 times the wavelength of the desired operating frequency is again used; however, it also has provisions for shorting out successive turns (moving from ends toward middle of the coil) on each end of the coil. With the patient's arm inserted, using low power, the shorting means would be successively applied in pairs (at each end) across the turns until the SWR meter nulls. (Shorting two adjacent end turns together effectively shortens the coil wire length by the circumference of a turn). At the null, coil wire length resonance exists at full wave operation and power is applied for treatment. (3) If the desired operating frequency is not fixed, then another alternative exists for realizing coil wire length resonance. The SWR meter is again observed using low rf power. By changing the frequency the SWR meter will null. Once it does it will be observed that once again the operating frequency is dependent on the length of wire used in winding the coil. However, in this case frequency is changed while wire length remains fixed. A different load (either in its electrical properties or size) will use a different frequency of operation. However, the wire length of the coil will still fall in the range of 0.7 to 1.3 of the final operating frequency wavelength.

Once coil wire length resonance is obtained (by any of the above means) for a given load, the coil can then be operated, if desired, at half-wavelength (using ½ the full wave operating frequency) and at other integral multiples of half-wavelength, the result being a shift of the heat focus volume axially along the length of the coil.

Under wire-length resonance conditions it has been found that for certain load-coil-frequency combinations no matching is necessary because the coil presents a 50-ohm resistive input to the associated rf generator. In the more general case, under other load-coil-frequency combinations only resistive matching is necessary, as the coil presents no reactive components to the rf generator at any ½ wavelength integral multiple of rf excitation. (Only at ½ wavelength excitation must a balanced input be used). No Balun transformer is necessary in connecting the coil's leads to the coaxial feed cable which then connects through the resistive matching network to the rf generator (via a second coaxial cable). The coaxial cables provide for radiation protection of operators and minimum interference to other electronic equipment. Both are used when operating at other than one-half wavelength (where only one can be used).

Coils have been employed in tests, using simulated fat-muscle phantoms as loads, at frequencies ranging from 7.5 to 62 MHz, for example, with internal coil diameters ranging from 7.6 cm (3 inches) to 40.6 cm (16 inches). Uniform deep-heating in a focussed volume was obtained for all designs according to the present invention. Using the design technique according to the invention, one can select any desired operating (excitation) frequency (of primary interest are those of the Instrumentation, Scientific and Medical Bands, centered at 13.56, 27.12 and 40.68 MHz), and for a desired treatment volume, achieve the same degree of heating in the same amount of time for a given load. In other words, heating rate is primarily dependent on the tissue conductivity at the operating frequency which, for the muscle phantom material used, does not change over this frequency range.

To maintain uniform heating at full wave operation, the coil length is preferably at least four times the coil diameter. At half-wave operation, the coil length is preferably at least twice the coil diameter.

Accordingly, a main object of the present invention is to overcome the deficiencies and disadvantages of previously known diathermy systems, such as the deficiencies and disadvantages mentioned above.

A further specific object of the invention is to provide an improved diathermy apparatus especially suited for applications to cancer therapy wherein the limb or trunk of a patient is received in a diathermy coil support, and wherein substantially uniform deep-heating is provided for the tissue in the interior portion of the receiving enclosure without excessively heating the surface tissue of the patient's limb or trunk received therein.

A still further object of the invention is to provide an improved diathermy apparatus of the type wherein an rf generator is connected to a limb- or trunk-receiving diathermy coil, wherein maximum power transfer from the rf generator is achieved, and wherein a unique wire-length resonance condition is employed to focus heat along the axis of the coil.

A still further object of the invention is to provide an improved diathermy apparatus for rf diathermy treatment wherein the patient's limb or trunk is received in a diathermy coil connected to the output of an rf generator and wherein a substantially uniform cross-sectional heating pattern is obtained, with minimal surface heating, and wherein the heating pattern is especially suitable for hyperthermia treatment in cancer therapy, providing maximum muscle (which lies under a fat layer in humans) heating so that the fat layer is heated less than the muscle, and wherein a relatively high heating rate is provided substantially uniformly throughout the muscle, thereby enabling successful hyperthermia treatment of cancer.

A still further object of the invention is to provide an improved diathermy treatment limb- or trunk-receiving coil assembly employing the principle of coil wire-length resonance, namely, which is dependent on the length of wire used to wind the coil, relative to the wavelength of the excitation rf generator, operating in the region above self-resonance of the coil, specifically, wherein the coil wire length is equal to 0.7 to 1.3 times (dependingon tissue electrical properties and volume) the operating wavelength, and wherein the amount of externally emitted radiation is relatively low, thereby reducing risks to operating personnel working in close proximity to the diathermy equipment, and also minimizing interference potential to other electronic or communication equipment.

BRIEF DESCRIPTION OF THE DRAWINGS

Further objects and advantages of the invention will become apparent from the following description and claims, and from the accompanying drawings, wherein:

DETAILED DESCRIPTION OF A PREFERRED EMBODIMENT

Figure 1:
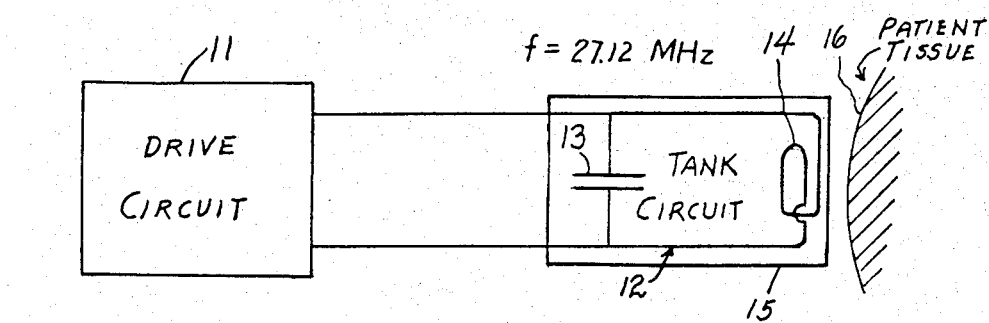
FIG. 1 is a schematic block diagram of a typical diathermy apparatus of the prior art.
Figure 2:
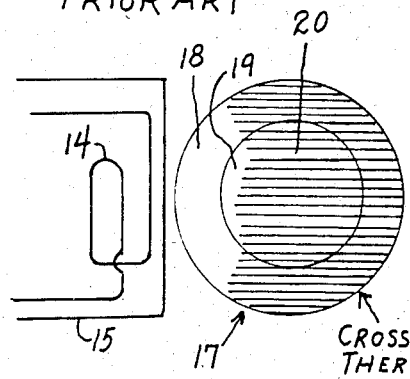
FIG. 2 is a replica of a thermographic camera recording substantially showing the cross-sectional heat distribution through the diathermy coil transmission area of the prior art apparatus of FIG. 1.
Figure 3:
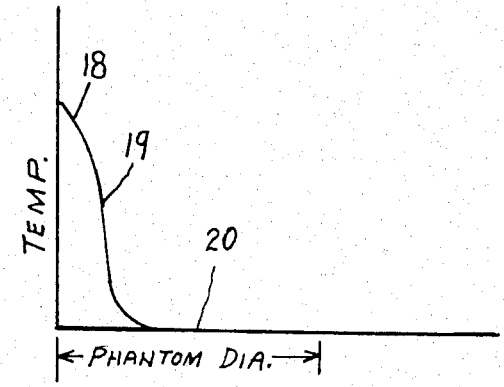
FIG. 3 is a graph substantially showing the diametrical heat distribution pattern of the replica of the thermographic camera recording of FIG. 2.

Referring to the drawings, and more particularly to FIGS. 1, 2 and 3, a typical prior art diathermy apparatus, basically similar to that disclosed in the U.S. Pat. No. 3,747,013 to H. C. Mettler, comprises a drive circuit 11 connected to a tank circuit 12 consisting of a tank capacitor 13 connected in parallel with a diathermy coil 14, tuned to generate output rf energy in an appropriate statutory diathermy band, centered for example at 27.12 MHz. The coil 14 is provided with a cover 15 and applies the output energy to a desired area 16 of a patient's body for heating said area and the tissue subjacent thereto. Designated at 17 in FIG. 2 is a replica of a thermogram recorded in the laboratory, showing the typical cross-sectional heating pattern obtained in the tissue region heated by coil 14 in the arrangement illustrated in FIG. 1. It will be seen that the cross-sectional heating pattern detected by the thermographic camera through the coil transmission area after 5 minutes of exposure shows a high temperature region 18 at the surface of the phantom immediately adjacent to the applicator, falling through a cooler region just under the fat layer and a central non-heated region in the phantom muscle, designated respectively at 19 and 20. This is graphically illustrated in FIG. 3, which shows the diametrical temperature distribution corresponding to the thermogram 17. This distribution pattern provides no heating in the center portion of the treated area and excessive heating on the surface. (If the coil 14 could be rearranged to receive a limb for hyperthermia treatment of a muscle, for example, the fat surrounding the muscle would still be the hottest part of the thermal distribution pattern, with no central heating of the muscle phantom because the coil wire length and coil length are too short and have too few turns, which would not be desirable for hyperthermia treatment).

Figure 4:
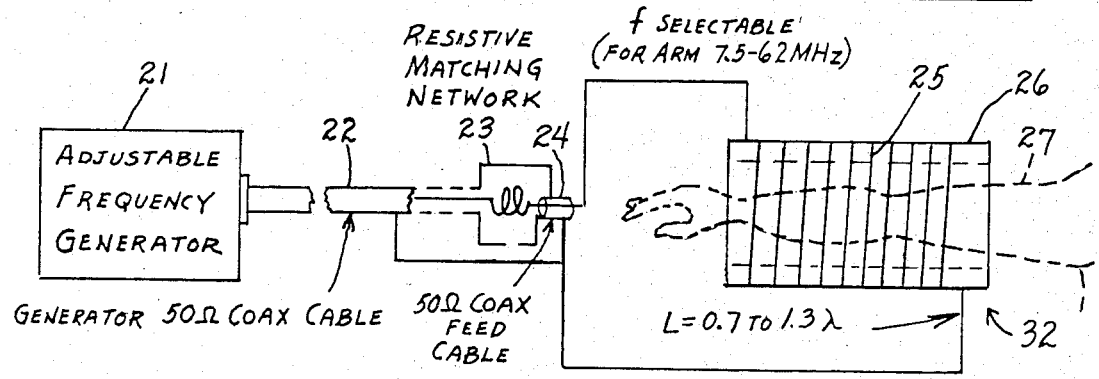
FIG. 4 is a schematic block diagram of a diathermy apparatus according to the present invention.
Figure 5:
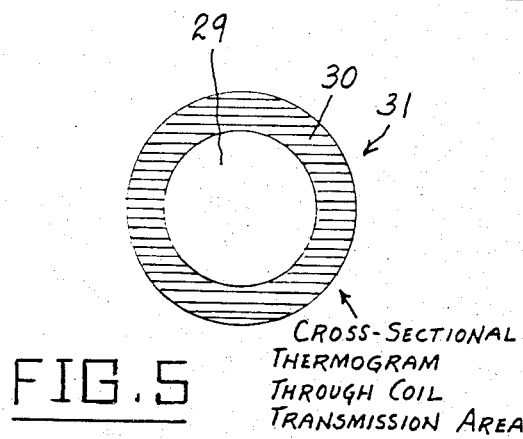
FIG. 5 is a replica of a thermographic camera recording substantially showing the cross sectional heat distribution through the improved diathermy coil transmission area of the apparatus of FIG. 4.
Figure 6:
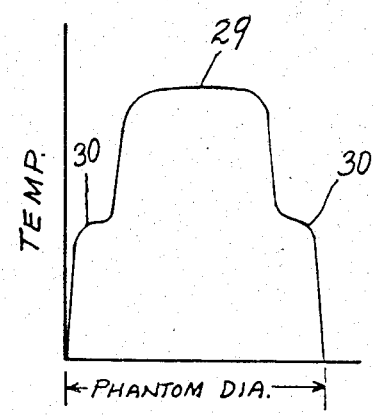
FIG. 6 is a graph substantially showing the diametrical heat distribution pattern corresponding to the replica of the thermographic recording of FIG. 5.

In contrast to FIGS. 1 to 3, FIG. 4 schematically shows an arrangement for hyperthermia treatment with diathermy apparatus according to the present invention. In the system of FIG. 4, an rf generator 21 delivers rf energy via a 50-ohm coaxial generator cable 22 through the resistive matching network 23 and through the coaxial feed cable 24 to a load comprising a special limb- or trunk-receiving coil 25 surrounding a tubular member 26, the load being suitably matched to the rf excitation source by a resistive (no reactive matching is necessary under coil wire length resonance operation) matching network 23. The tubular member 26 is adapted to receive, for example, a patient's limb 27 for hyperthermia treatment. Due to the construction of the coil 25, presently to be described, the heating distribution pattern is similar to that shown in FIG. 5, showing a replica 31 of a cross-sectional thermogram recorded through the coil transmission area in an actual design according to the present invention, wherein the large central area 29, after 4 minutes of exposure, was substantially uniform at a high temperature, and wherein the annular outer area 30, corresponding to the location of the fat layer surrounding the muscle, was at a considerably cooler temperature. This is graphically illustrated in FIG. 6, which shows the diametrical temperature distribution corresponding to the thermogram 31 of FIG. 5.

Figure 7:
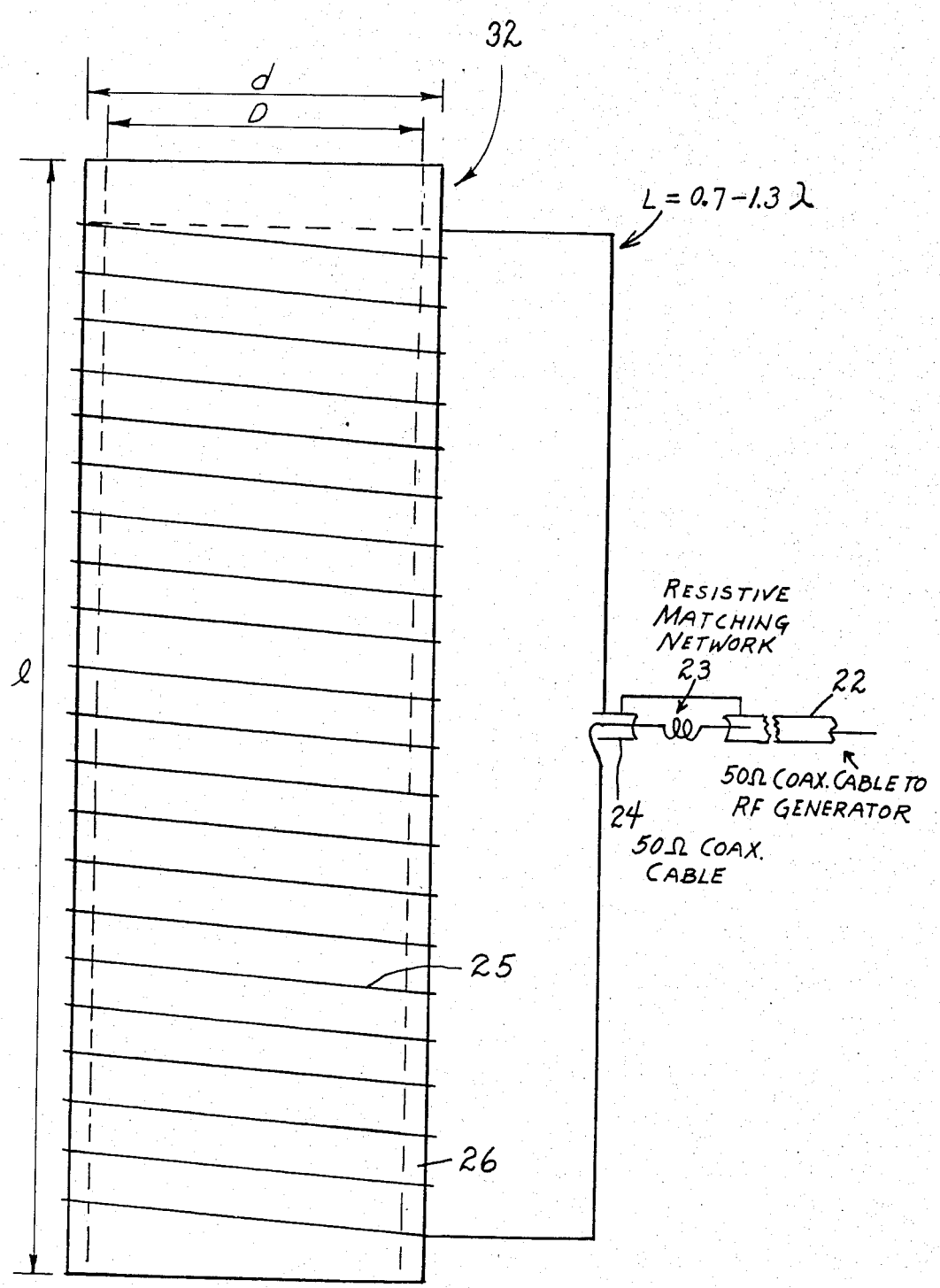
FIG. 7 is a schematic diagram of a typical diathermy coil load circuit corresponding to FIG. 4, showing the diathermy coil in elevational view, corresponding to a specific embodiment of a diathermy coil of the present invention.

FIG. 7 shows a typical limb-receiving hyperthermia treatment coil assembly, designated at 32, which may be employed in the diathermy apparatus of FIG. 4. The tubular member 26 has a diameter D sufficiently large to comfortably receive the limb or other body part to be treated. The tubular member 26 may be used as a support for the coil 25, said coil being helically wound thereon with uniform spacing between the turns. To maintain uniform heating at full-wave operation, the coil length l is preferably at least four times the coil diameter d. Coils have been designed for use at frequencies preferably ranging from 7.5 to 62 MHz (although the design is not limited to this range) with internal diameters ranging from 7.6 cm (3 inches) to 50.8 cm (20 inches). In each design, the length L of wire used for the coil 25, as opposed to the coil length l itself, is 0.7 to 1.3 (depending on the specific electrical properties and volume of the phantom used) times the free-space wavelength of the operating frequency. The coils may also be operated at half-wavelength and at integral multiples of half-wavelength, the result being a shift of the heat focus volume axially along the coil.

Under the above conditions of wire length resonance it has been demonstrated that for certain load-coil-frequency combinations, no matching is necessary because the coil 25 presents a 50-ohm resistive input to the rf generator 21. In the more general case, under other load-coil-frequency combinations, only resistive matching is necessary, as the coil 25 presents no reactive components to the rf generator 21 at any half-wavelength integral multiple of rf excitation. (Only at one half-wavelength excitation must a balanced input be used). No Balun transformer is necessary in connecting the coil's leads through the coaxial feed cable 24 to the resistive matching network 23 and through the coaxial generator cable 22. The coaxial cables are used for radiation protection of the operators and interference suppression to other electronic equipment and communication systems when operating at other than one half-wavelength, and for this reason full-wavelength operation is preferred.

In operation, the apparatus produces uniform deep-heating in tissue (or other lossy dielectric material) at the desired location in the material being treated, without excessive heating of the surface tissue, and focusses the heating volume along the axis of the heating coil 25. Operation is at coil wire-length resonance, as opposed to the commonly known self-resonance of the coil.

The thermogram of which FIG. 5 is a replica was taken using a standard cylindrical, fat-simulating, hollow arm diathermy phantom filled with muscle-simulating material, inserted in the coil, the diathermy phantom being in two identical cylindrical half-sections abutting at a midplane. After the test heating period, one cylindrical half-section of the muscle-filled phantom was removed and the midplane surface of the remaining half-section was viewed with the thermographic camera. The overall heating of the cross-section was shown as a thermogram and was similar to FIG. 5. This data was obtained using a frequency of 27.12 MHz. The coil wire length used to obtain coil wire length resonance at full wave operation at a frequency of 27.12 MHz was 0.75 times the free space wavelength of the operating frequency ($\lambda = 1106$ cm), or 830 cm. The thermogram of FIG. 2 was obtained in a similar manner but in a system similar to that of FIG. 1.

An important feature of the operation of coil 25 is that under the herein-specified conditions the coil is a very inefficient antenna in terms of emitting radiation. Low emission is an important safety consideration, since personnel should not be exposed to excessive levels of radiation while working in close proximity to the system. Being an inefficient radiator, however, results in its being a very efficient heater of dielectric materials inserted in the coil, while minimizing its potential to interfere with other electrical or communications systems.

The rf generator 21 is of a conventional type adjustable to provide output frequencies corresponding to integral multiples of one half of the basic fundamental wavelength for which coil 25 is designed, whereby to enable modification of the axial distribution of the heat developed in the material received in the coil. At full wave operation, using said basic fundamental wavelength, the heat will be substantially localized at the central portion of the coil axis. As above mentioned, half-wavelength, or integral multiples of half-wavelength may be employed to shift the heat focus volume axially along the coil.

While a specific embodiment of an improved diathermy apparatus has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. A diathermy apparatus comprising elongated hollow support means adapted to receive dielectric material to be heated, a coil surrounding said elongated support means substantially coaxially and comprising a plurality of turns, radio frequency generator means providing an output frequency in the range of from 7.5 MHz to 62 MHz, and means for connecting the output of said generator means to said coil, only the coil and the contents of said hollow support means acting as a load, the total wire length of said coil being about 0.7 to 1.3 times the fundamental wavelength corresponding to said output frequency.

2. The diathermy apparatus of claim 1, and wherein said turns are spaced substantially evenly along said elongated hollow support means.

3. The diathermy apparatus of claim 1, and wherein said elongated support means comprises a cylindrical tube and wherein said coil comprises evenly spaced helical turns extending along the cylindrical tube.

4. The diathermy apparatus of claim 1, and wherein the longitudinal length of the coil is at least twice its diameter, for half-wave operation.

5. The diathermy apparatus of claim 1, and wherein the longitudinal length of the coil is at least four times its diameter, for full wave operation.

6. The diathermy apparatus of claim 1, and wherein said means connecting the output of said generator means to said coil comprises two coaxial transmission cables connected respectively to the generator means and the terminals of the coil, and resistive impedance matching means connected between the generator means coaxial cable and the coaxial cable connected to the terminals of the coil.

7. The diathermy apparatus of claim 1, and wherein said hollow support means comprises a cylindrical member, said coil having its turns evenly spaced along said cylindrical member, and wherein the longitudinal length of the coil is at least twice its diameter, for half-wave operation.

8. The diathermy apparatus of claim 7, and wherein the longitudinal length of the coil is at least four times its diameter, for full-wave operation.

9. The diathermy apparatus of claim 7, and wherein the coil has an inside diameter in the range between 7.6 cm and 50.8 cm.

10. The diathermy apparatus of claim 1, and wherein said radio frequency generator means includes means for adjusting the output frequencies corresponding to integral multiples of one half of said fundamental wavelength, for modifying the axial distribution of the heat developed in the material received in the support means.

11. The apparatus according to claim 1, and further including means for minimizing extraneous emitted radiation, whereby the risk of exposure to personnel and interference with electronic and communications equipment is minimized.

12. Apparatus for providing axially focussed, uniform deep heating for a portion of a body, such as a limb, comprising:
    hollow support means for supporting said body portion;
    a coil surrounding, and supported by, said support means;
    radio frequency generator means providing an output frequency of between 7.5 MHz and 62 MHz;
    and means for connecting the output of said generator means to said coil, only the coil and the contents of said hollow support means acting as a load, the total length of said coil wire being 0.7 to 1.3 times the fundamental wavelength of the output frequency so that heat is focussed along the axis of the coil.

13. A method of heating a dielectric material comprising inserting the material in a coil and energizing said coil with current at a radio frequency in the range of from 7.5 MHz to 62 MHz, the coil having a wire length about 0.7 to 1.3 times that of the wavelength of said radio frequency, whereby to develop heat in said material at a first location along the axis of the coil, and modifying the axial distribution of the developed heat by energizing the coil with a radio frequency current corresponding to an integral multiple of a half-wavelength of said first-named wavelength.

14. A method according to claim 13, and selecting the operating frequency so as to maintain suitable coil size and wire length resonance operating conditions for focussed delivery of uniform cross-sectional heating.

* * * * *